(12) United States Patent
Luitjens et al.

(10) Patent No.: US 10,041,049 B2
(45) Date of Patent: Aug. 7, 2018

(54) METHOD FOR THE PRODUCTION OF ADENOVIRAL VECTORS

(75) Inventors: Alfred Luitjens, Leiden (NL); John A. Lewis, Little Compton, RI (US)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 13/126,978

(22) PCT Filed: Oct. 29, 2009

(86) PCT No.: PCT/EP2009/064265
§ 371 (c)(1),
(2), (4) Date: Apr. 29, 2011

(87) PCT Pub. No.: WO2010/060719
PCT Pub. Date: Jun. 3, 2010

(65) Prior Publication Data
US 2011/0207202 A1    Aug. 25, 2011

Related U.S. Application Data

(60) Provisional application No. 61/198,122, filed on Nov. 3, 2008.

(30) Foreign Application Priority Data

Nov. 3, 2008  (EP) .................................. 08168181

(51) Int. Cl.
| | | |
|---|---|---|
| C12N 15/00 | (2006.01) | |
| A01N 63/00 | (2006.01) | |
| A61K 35/76 | (2015.01) | |
| A61K 39/002 | (2006.01) | |
| A61K 39/235 | (2006.01) | |
| C12N 7/00 | (2006.01) | |

(52) U.S. Cl.
CPC ...... C12N 7/00 (2013.01); *C12N 2710/10343* (2013.01); *C12N 2710/10351* (2013.01)

(58) Field of Classification Search
CPC .......... C12N 15/86; C12N 2710/10343; A61K 35/761; A61K 38/02
USPC ...................................................... 435/239
See application file for complete search history.

(56) References Cited

U.S. PATENT DOCUMENTS

| | | | |
|---|---|---|---|
| 5,261,823 A | 11/1993 | Kurokawa | |
| 5,559,099 A | 9/1996 | Wickham et al. | |
| 5,837,511 A | 11/1998 | Falck-Pedersen et al. | |
| 5,837,520 A | 11/1998 | Shabram et al. | |
| 5,846,782 A | 12/1998 | Wickham et al. | |
| 5,851,806 A | 12/1998 | Kovesdi et al. | |
| 5,891,690 A | 4/1999 | Massie | |
| 5,965,541 A | 10/1999 | Wickham et al. | |
| 5,981,225 A | 11/1999 | Kochenek et al. | |
| 5,994,106 A | 11/1999 | Kovesdi et al. | |
| 5,994,128 A | 11/1999 | Fallaux et al. | |
| 6,020,191 A | 2/2000 | Scaria et al. | |
| 6,040,174 A | 3/2000 | Imler et al. | |
| 6,113,913 A | 9/2000 | Brough et al. | |
| 6,261,823 B1 | 7/2001 | Tang et al. | |
| 6,485,958 B2 | 11/2002 | Blanche et al. | |
| 6,492,169 B1 | 12/2002 | Vogels et al. | |
| 6,537,793 B2 | 3/2003 | Blanche et al. | |
| 6,544,424 B1 | 4/2003 | Shevitz | |
| 6,586,226 B2 | 7/2003 | Carrion et al. | |
| 6,869,794 B2 | 3/2005 | Vogels et al. | |
| 6,913,922 B1 | 7/2005 | Bout et al. | |
| 6,974,695 B2 | 12/2005 | Vogels et al. | |
| 7,125,706 B2 | 10/2006 | Zhang et al. | |
| 7,235,233 B2 | 6/2007 | Havenga et al. | |
| 7,250,293 B2 | 7/2007 | Vogels et al. | |
| 7,270,811 B2 | 10/2007 | Vogels et al. | |
| 7,300,657 B2 | 11/2007 | Pau et al. | |
| 7,344,883 B2 | 3/2008 | Vogels et al. | |
| 7,387,894 B2 | 6/2008 | Pau et al. | |
| 7,468,181 B2 | 12/2008 | Vogels et al. | |
| 7,521,229 B2 | 4/2009 | Pau et al. | |
| 7,524,947 B2 | 4/2009 | Pau et al. | |
| 7,598,078 B2 | 10/2009 | Havenga et al. | |
| 7,629,167 B2 | 12/2009 | Hodge et al. | |
| 7,741,099 B2 | 6/2010 | Havenga et al. | |
| 7,816,104 B2 | 10/2010 | Vogels et al. | |
| 7,820,440 B2 | 10/2010 | Vogels et al. | |
| 7,867,764 B2 | 1/2011 | Pau et al. | |
| 7,906,113 B2 | 3/2011 | Bout et al. | |
| 8,546,123 B2 | 10/2013 | Lewis | |
| 9,022,240 B2 | 5/2015 | Lewis | |
| 2003/0215948 A1 | 11/2003 | Kaleko et al. | |

(Continued)

FOREIGN PATENT DOCUMENTS

| | | |
|---|---|---|
| EP | 0853660 | 7/1997 |
| EP | 1230354 | 11/2000 |

(Continued)

OTHER PUBLICATIONS

Yuk et al., Perfusion Cultures of Human Tumor Cells: A Scalable Production Platform for Oncolytic Adenoviral Vectors, 2004, Biotechnology and Bioengineering, 86(6):637-642).*
Subramanian et al. "Pilot-scale adenovirus seed production through concurrent virus release and concentration by hollow fiber filtration", 2005, Biotechnology Progress, 21:851-859.*
Zhang et al., "A two-stage bioreactor system for the production of recombinant proteins using a genetically engineered baculovirus/ insect cell system", 1993, Biotechnology and Bioengineering, 42:357-366.*
Dai et al., Comparative study of the replication difference of HearNPV in infected exponential and stationary host cells, 2007, 23:pdf p. 1.*
Altaras et al; Production and Formulation of Adenovirus Vectors; Advances in Biochemical Engineering, vol. 99, Nov. 1, 2005; pp. 193-260.

(Continued)

*Primary Examiner* — Barry A Chestnut
(74) *Attorney, Agent, or Firm* — TraskBritt, P.C.

(57) ABSTRACT

The invention provides methods for large-scale production of recombinant adenovirus 35, using perfusion systems and infection at very high-cell densities.

27 Claims, 3 Drawing Sheets

(56) References Cited

U.S. PATENT DOCUMENTS

| | | |
|---|---|---|
| 2004/0002060 A1 | 1/2004 | Kaleko et al. |
| 2004/0043489 A1 | 3/2004 | Havenga et al. |
| 2005/0153420 A1 | 7/2005 | Konz, Jr. et al. |
| 2005/0158278 A1 | 7/2005 | Vogels et al. |
| 2005/0196384 A1 | 9/2005 | Vogels et al. |
| 2005/0196854 A1 | 9/2005 | Konz, Jr. et al. |
| 2005/0232900 A1 | 10/2005 | Vogels et al. |
| 2005/0265974 A1 | 12/2005 | Pau et al. |
| 2007/0071726 A1 | 3/2007 | Pau et al. |
| 2007/0088156 A1 | 4/2007 | Pau et al. |
| 2007/0178115 A1 | 8/2007 | Tang et al. |
| 2007/0207461 A1 | 9/2007 | Weggeman et al. |
| 2008/0118970 A1 | 5/2008 | Konz, Jr. et al. |
| 2008/0124360 A1 | 5/2008 | Seggern |
| 2008/0131461 A1 | 6/2008 | Pau et al. |
| 2008/0153083 A1 | 6/2008 | Vogels et al. |
| 2008/0171018 A1 | 7/2008 | Bout et al. |
| 2008/0199433 A1 | 8/2008 | Vogels et al. |
| 2008/0199917 A1 | 8/2008 | Vogels et al. |
| 2008/0199939 A1 | 8/2008 | Havenga et al. |
| 2008/0206837 A1 | 8/2008 | Vogels et al. |
| 2008/0220014 A1 | 9/2008 | Pau et al. |
| 2009/0017523 A1 | 1/2009 | Weggeman et al. |
| 2009/0035856 A1 | 2/2009 | Galliher et al. |
| 2009/0123989 A1 | 5/2009 | Weggeman |
| 2009/0175897 A1 | 7/2009 | Tang et al. |
| 2009/0285879 A1 | 11/2009 | Pau et al. |
| 2010/0015176 A1 | 1/2010 | Vogels et al. |
| 2010/0034774 A1 | 2/2010 | Vogels et al. |
| 2010/0055166 A1 | 3/2010 | Voss |
| 2010/0062028 A1 | 3/2010 | Cohen et al. |
| 2010/0143302 A1 | 6/2010 | Havenga et al. |
| 2010/0150998 A1 | 6/2010 | Cohen et al. |
| 2010/0172928 A1 | 7/2010 | Pau et al. |
| 2010/0311172 A1 | 12/2010 | Vogels et al. |
| 2011/0081377 A1 | 4/2011 | Roederer et al. |
| 2012/0315696 A1 | 12/2012 | Luitjens et al. |

FOREIGN PATENT DOCUMENTS

| | | |
|---|---|---|
| EP | 1816204 A1 | 8/2007 |
| WO | WO 96/26281 | 8/1996 |
| WO | WO 97/08298 | 3/1997 |
| WO | WO 98/22588 | 5/1998 |
| WO | WO 98/39411 | 9/1998 |
| WO | WO 99/12568 | 3/1999 |
| WO | WO 99/41416 | 8/1999 |
| WO | WO 00/03029 | 1/2000 |
| WO | WO 00/29024 | 5/2000 |
| WO | WO 00/50573 | 8/2000 |
| WO | WO 00/70071 | 11/2000 |
| WO | 0136615 A2 | 5/2001 |
| WO | WO 01/66137 | 9/2001 |
| WO | WO 02/40665 | 5/2002 |
| WO | WO 02/44348 | 6/2002 |
| WO | WO 03/049763 | 6/2003 |
| WO | WO 03/078592 | 9/2003 |
| WO | WO 03/097797 | 11/2003 |
| WO | WO 03/104467 | 12/2003 |
| WO | WO 04/055187 | 7/2004 |
| WO | WO 05/080556 | 9/2005 |
| WO | WO2005080556 * | 9/2005 |
| WO | WO2005095578 * | 10/2005 |
| WO | WO 06/053871 | 5/2006 |
| WO | 2006086284 A2 | 8/2006 |
| WO | WO 06/108707 | 10/2006 |
| WO | WO 07/10409 | 1/2007 |
| WO | 2007104792 A2 | 9/2007 |
| WO | 2007110409 A1 | 10/2007 |
| WO | 2009064265 A1 | 5/2009 |
| WO | 2010060719 A1 | 6/2010 |
| WO | 2011045381 A1 | 4/2011 |
| WO | 2011098592 A1 | 8/2011 |

OTHER PUBLICATIONS

Havenga et al; Novel replication-incompetent adenoviral B-group vectors: high vector stability and yield in PER.C6 cells; Journal of General Virology, Society for General Microbiology; vol. 87, No. Part 8; Aug. 1, 2006; pp. 2135-2143.

Henry et al; Insights into adenoviral vector production kinetics in acoustic filter-based perfusion cultures; Biotechnology and Bioengineering; vol. 86, No. 7; Jun. 30, 2004; pp. 765-774.

International Preliminary Report on Patentability; PCT/EP2009/064265; dated Sep. 2, 2010.

International Search Report; PCT/EP2009/064265 dated Dec. 4, 2009.

Maranga et al; Characterization of changes in PER.C6™ cellular metabolism during growth and propagation of a replication-deficient adenovirus vector; Biotechnology and Bioengineering; vol. 90; No. 5; Jun. 1, 2005; pp. 645-655.

Subramanian et al; Pilot-scale adenovirus seed production through concurrent virus release and concentration by hollow fiber filtration; Biotechnology Progress; May/Jun. 2005; vol. 21, No. 3; May 2005; pp. 851-859.

Xie et al; Large-scale propagation of a replication-defective adenovirus vector in stirred-tank bioreactor PER.C6TM cell culture under sparging conditions; Biotechnology and Bioengineering; vol. 83, No. 1; Jul. 5, 2003; pp. 45-52.

Yallop et al; Per.C6 cells for the manufacture of biopharmaceutical proteins; Modern Biopharmaceuticals: Design Development and Optimazation; vol. 3; Jan. 1, 2005; pp. 779-807.

Yuk et al; Perfusion cultures of human tumor cells: A scalable production platform for oncolytic adnoviral vectors; Biotechnology and Bioengineering, Wiley & Sons, vol. 86, No. 6; Jun. 20, 2004; pp. 637-642.

Yamada et al., Adenovirus vector production using low-multiplicity infection of 293 cells, Cytotechnology, 2009, pp. 153-160, vol. 59.

Shen et al., Reassessing Culture Media and Critical Metabolites that Affect Adenovirus Production, Biotechnol. Prog., 2010, pp. 200-207, vol. 26, No. 1, Wiley InterScience.

Lee et al., Low-Glutamine Fed-Batch Cultures of 293-HEK Serum-Free Suspension Cells for Adenovirus Production, Biotechnol. Prog., 2003, pp. 501-509, vol. 19, American Chemical Society and American Institute of Chemical Engineers.

Cortin et al., High-Titer Adenovirus Vector Production in 293S Cell Perfusion Culture, Biotechnol. Prog. 2004, pp. 858-863, vol. 20, American Chemical Society and American Institute of Chemical Engineers.

Kamen et al., Development and optimization of an adenovirus production process, The Journal of Gene Medicine, J. Gene Med. 2004, pp. S184-S192, vol. 6, John Wiley & Sons, Ltd.

Berdichevsky et al. Establishment of Higher Passage PER.C6 Cells for Adenovirus Manufacture, Biotechnol. Prog. 2008, pp. 158-164, vol. 24.

Havenga et al., Serum-Free Transient Protein Production System Based on Adenoviral Vector and PER.C6 Technology: High Yield and Preserved Bioactivity, Biotechnology and Bioengineering, Jun. 1, 2008, pp. 273-283, vol. 100, No. 2, Wiley Periodicals, Inc.

Radosevic et al., Protective Immune Responses to a Recombinant Adenovirus Type 35 Tuberculosis Vaccine in Two Mouse Strains: CD4 and CD8 T-Cell Epitope Mapping and Role of Gamma Interferon, Infection and Immunity, Aug. 2007, pp. 4105-4115, vol. 75, No. 8.

Liu et al., A high-yield and scaleable adenovirus vector production process based on high density perfusion culture of HEK 293 cells as suspended aggregates, Journal of Bioscience and Bioengineering, pp. 524-529, vol. 107, The Society of Biotechnology, Japan.

Kovesdi et al., Adenoviral Producer Cells, Viruses, 2010, pp. 1681-1703, vol. 2.

Luitjens, Alfred, Intensifying the Productivity of a Recombinant AD35 Manufacturing Process Using the PER.C6® Cell Substrate, Presentation at Vaccine Technology II Program, Jun. 1-6, 2008, at Grande Real Santa Eulalia Resort, Albufeira, Algarve, Portugal.

Abbink et al., Comparative Seroprevalence and Immunogenicity of Six Rare Serotype Recombinant Adenovirus Vaccine Vectors from Subgroups B and D, Journal of Virology, May 2007, pp. 4654-4663m vol. 81, No. 9.

(56) References Cited

OTHER PUBLICATIONS

Bleckwenn et al., Production of Recombinant Protein Using the HeLa S3-Vaccinia Virus Expression System: Bioreactor Perfusion and Effects of Post-Infection Temperature, Biosci. Biotechnol. Biochem., 2005, pp. 1065-1072, vol. 69, No. 5.

Chartrain et al., Development and Production of Commercial Therapeutic Monoclonal Antibodies in Mammalian Cell Expression Systems: An Overview of the Current Upstream Technologies, Current Pharmaceutical Biotechnology, 2008, pp. 447-467.

Derwent Acc No: 2008-J31941, New human adenovirus serotype 26 (Ad26), is useful for treating, preventing, or diagnosing infection, copyright date 2012.

Estape et al., Comparison of campaign vs concurrent large-scale cell culture facilities. Pharmaceutical Engineering. vol. 26, No. 5, Sep./Oct. 2006.

Furey J., Scale-up of a cell culture perfusion process A low-shear filtration system that inhibits filter-membrane fouling. Genetic Engineering News. vol. 22, No. 7, Apr. 2002.

Heidemann et al., A new seed-train expansion method for recombinant mammalian cell lines, Cytotechnology, 2002, pp. 99-108, vol. 38.

Shott et al., Adenovirus 5 and 35 vectors expressing Plasmodium falciparum circumsporozoite surface protein elicit potent antigen-specific cellular IFN-gamma and antibody responses in mice. Vaccine 26: 2818-2823 (2008).

Wang et al., Using QPCR to assign infectious potencies to adenovirus based vaccines and vectors for gene therapy: toward a universal method for the facile quantitation of virus and vector potency. Vaccine 23: 4500-4508 (2005).

Xie et al., Serum-Free Suspension Cultivation of PER.C6® Cells and Recombinant Adenovirus Production Under Different pH Conditions, Biotechnology and Bioengineering, 2002, pp. 569-570, vol. 80, No. 5.

\* cited by examiner

METHOD FOR THE PRODUCTION OF ADENOVIRAL VECTORS

CROSS-REFERENCE TO RELATED APPLICATIONS

This is a national phase entry under 35 U.S.C. § 371 of International Patent Application PCT/EP2009/064265, filed Oct. 29, 2009, published in English as International Patent Publication WO 2010/060719 A1 on Jun. 3, 2010, which claims the benefit under Article 8 of the Patent Cooperation Treaty and 35 U.S.C. § 119(e) to U.S. Provisional Patent Application Ser. No. 61/198,122, filed Nov. 3, 2008, and European Patent Application Serial No. 08168181.9, filed Nov. 3, 2008.

TECHNICAL FIELD

The invention relates to the field of cell culture and adenovirus production. More particularly, it concerns improved methods for the culturing of mammalian cells, infection of those cells with adenovirus and the production of adenovirus particles therefrom.

BACKGROUND

Recent developments in the field of DNA vaccination using recombinant viral vectors have created the need for large scale manufacturing of clinical grade material. Processes are needed to be able to support the less and least developed world with sufficient amounts of recombinant adeno-based vaccines to fight, e.g., the Tuberculosis and Malaria problem in the world. An evaluation of the birth cohort shows that more than 150,000,000 births are expected for the less and least developed world in 2010-2015. Based on this birth cohort, the projected annual demand for a vaccine could reach approximately $1.5 \times 10^{19}$ virus particles (VP) on a yearly basis.

Several processes for production of adenoviruses have been described. These processes use adherent cell cultures in roller bottles, cell factories (Nunclon from Nunc or CellStack from Corning), or Cell Cubes (Corning). Production processes on adherent cell cultures cannot fulfill the world-wide demand for adeno-based vaccines. Therefore, the cells used in the adherent process are adapted to suspension cultures (e.g., HEK293 and PER.C6® cell lines). With the use of suspension cultures it is possible to scale-up production processes to large-scale bioreactors. Suspension cell cultures for adenovirus production are routinely achieved between 3 to 20 L scale and successful scale-up has been reported up to 100 L (Kamen et al., 2004), and 250 L (Xie et al., 2003). Experiments are reported in which scaling up to 10,000 L is anticipated (Xie et al., 2003).

However, a major disadvantage of scaling up to 10,000 L is the high capital investment (CAPEX), which is needed to design and build a 10,000 L bioreactor facility. Furthermore, the CAPEX commitment of building a 10,000 L facility, under BSL 2 conditions, must be realized before even knowing if the product will be successful (Phase IV and beyond). The total investment cost for a 10,000 L bioreactor plant is reported between € 225,000,000 and € 320,000,000 (Estape et al., 2006). Therefore, preparation at lower scale, e.g., in 1000 L or smaller bioreactors, would be desirable.

With the use of currently existing processes, more than 150 batches at 1000 L scale a year must be produced in order to reach the target of $1.5 \times 10^{19}$ VP/year. Therefore, a need exists to improve systems for adenovirus production, to improve yields of adenovirus particles in order to fulfill the world-wide demand of adenovirus vaccines, preferably at non-prohibitive costs.

One of the issues encountered in adenovirus production optimization is the so-called "cell density effect." In batch-mode operation, several references suggest the existence of an optimal cell density at infection for adenovirus production. The optimum lies between $0.5-1 \times 10^6$ cells/mL (Maranga et al., 2005; Kamen et al., 2004). It was shown for adenovirus (Ad5) production in a batch stirred tank bioreactor that the virus productivity per cell remains constant up to around $0.9 \times 10^6$ cells/mL, but drops abruptly at around $1 \times 10^6$ cells/mL (Altaras et al., 2005). Beyond $2 \times 10^6$ cells/mL, no infectious particles were detectable. The breakpoint related to specific production drop with cell densities at infection is medium dependent. No available commercial medium to date has shown potential to support high yields of virus particles, while maintaining the specific production optimal at cell densities beyond $1 \times 10^6$ cells/mL (Kamen et al., 2004). The reasons for this drop are not known yet but might be due to limited nutrient availability for virus production, or due to high metabolites concentrations that are inhibitory for virus production.

Fed-Batch operations, like addition of glucose, glutamine and amino acids allowed infections at cell densities up to $2 \times 10^6$ cells/mL. However, the productivities attained at high-cell densities were lower than those obtained with infection at cell densities of $1 \times 10^6$ cells/mL (Kamen et al., 2004).

In perfusion processes, the cells are retained in the bioreactor by hollow fibers, spin filters or acoustic separators while culture medium is perfused through the bioreactor. In these processes cell densities of $>100 \times 10^6$ cells/mL can sometimes be reached (e.g., Yallop et al., 2005).

Infected perfusion cells showed premature cell loss during perfusion with a hollow fiber system. This might be related to their higher shear sensitivity due to the viral infection (Cortin et al., 2004). The hydro-dynamical stresses induced in the tubing, the hollow fibers, or the peristaltic pump on more fragile, infected cells was most likely the cause for this phenomenon. Since infected cells are more fragile, particularly the acoustic separator (Henry et al., 2004) has been suggested to be desirable if the perfusion is to be maintained throughout the infection phase. However, infections performed in perfusion mode could only be maintained for cell densities up to $3 \times 10^6$ cells/mL with a perfusion rate of 2 vol/day. Infection at a cell density of $6 \times 10^6$ cells/mL led to a fivefold reduction in specific productivity (Henry et al., 2004).

Despite the reported cell density effect by others, one report (Yuk et. al., 2004) described successful perfusion cultures of human tumor cells as a production platform for oncolytic adenoviral vectors. That report described a high-cell-density perfusion process using alternating tangential flow (ATF) technology. At an average viable cell density at an infection of $9 \times 10^6$ HeLaS3 cells/mL, an average viral titer of about $4 \times 10^{11}$ VP/mL was observed. The tumor cells used in that report are not preferred as production cells, since use of tumor cells may pose safety risks when the produced adenovirus particles are to be administered to humans. The recombinant adenovirus in that report was based on Ad5. Such adenoviruses have limited possibilities for use as vaccines since a majority of the human population has pre-existing neutralizing antibodies against Ad5, and recombinant adenoviruses from other serotypes are therefore more suitable for use as vaccines (see, e.g., WO 00/70071). In particular, recombinant adenoviruses from subgroup B, such as Ad35, are especially advantageous for use as vaccines (WO 00/70071).

Limited information, if any, is available for the large scale production of recombinant adenoviruses from other serotypes than Ad5, in particular for the advantageous serotype 35. Some differences between Ad35 and Ad5 have been described with respect to purification thereof using anion exchange (e.g., WO 2005/080556). The somewhat different physical properties of recombinant adenoviruses of different serotypes may give rise to differences in production processes or under certain conditions. Such potential differences may especially be important at industrial scale, where even seemingly small differences at small scale may have large economic consequences on the scale envisaged for production of the annual world-wide demand. For instance, it is hitherto unknown whether the reported cell density effect for Ad5 will be similar for other serotypes. Therefore, in order to fulfill the world-wide demand of rAd35 vaccines, a need exists to improve systems for recombinant adenovirus serotype 35 (rAd35) production.

DISCLOSURE

We have found herein that yields of recombinant adenovirus serotype 35 (rAd35) further increased when production cells were infected at densities beyond $10\times10^6$ viable cells/mL, in perfusion cultures. In contrast, the yields of recombinant adenovirus serotype 5 (rAd5) were lower when production cells where infected at $20\times10^6$ or $30\times10^6$ viable cells/mL compared to infection at $10\times10^6$ viable cells/mL. Thus, rAd35 propagates differently than rAd5 in the producer cells under the conditions employed. In addition we have seen that yet another serotype again behaves differently, suggesting that processes for specific adenovirus serotypes may have to be fine-tuned for each serotype, in order to obtain optimal results. The present invention provides an optimized system for production of rAd35 in terms of yield, quality of the rAd35 obtained, and ease of handling of the harvest for downstream processing.

Provided is a method for producing recombinant adenovirus serotype 35 (rAd35), the method comprising: a) culturing producer cells in suspension with a perfusion system; b) infecting the cells at a density of between about $10\times10^6$ viable cells/mL and $16\times10^6$ viable cells/mL with rAd35; c) further culturing the infected cells with a perfusion system to propagate the rAd35; and d) harvesting the rAd35.

In certain embodiments, the cells in step b) are infected with rAd35 at a density of between about $10\times10^6$ and $14\times10^6$ viable cells/mL.

In certain preferred embodiments, the perfusion system in step c) is an alternating tangential flow (ATF) perfusion system. In other preferred embodiments, the perfusion system in step a) is an alternating tangential flow (ATF) perfusion system. In a preferred embodiment, the perfusion system in both steps a) and c) is an alternating tangential flow (ATF) perfusion system.

In certain embodiments, the method of the invention further comprises: e) purifying the rAd35. In further embodiments, the method further comprises: f) preparing a pharmaceutical composition containing the purified rAd35.

In certain embodiments, the recombinant adenovirus lacks at least a portion of the E1 region, and comprises heterologous nucleic acid.

In preferred embodiments, the physical particle to infectious particle (VP/IU) ratio of the produced rAd35 is less than 30:1, preferably less than 20:1.

Also provided is a method for producing at least $1\times10^{12}$ rAd35 virus particles (VP)/mL, the method comprising: a) culturing producer cells in suspension with a perfusion system; b) infecting the cells at a density of between about $10\times10^6$ viable cells/mL and $16\times10^6$ viable cells/mL with rAd35; c) further culturing the infected cells with a perfusion system to propagate the rAd35, whereby the concentration of rAd35 virus particles reaches at least $1\times10^{12}$ VP/mL; and d) harvesting the rAd35.

Also provided is a bioreactor with a working volume of between 2 L and 1000 L, comprising: culture medium, producer cells, and at least $1\times10^{12}$ rAd35 virus particles (VP)/mL. In certain embodiments, the bioreactor has a working volume of between 50 L and 500 L. In preferred embodiments, the bioreactor is connected to an ATF perfusion system.

DETAILED DESCRIPTION OF THE INVENTION

Figure 1:
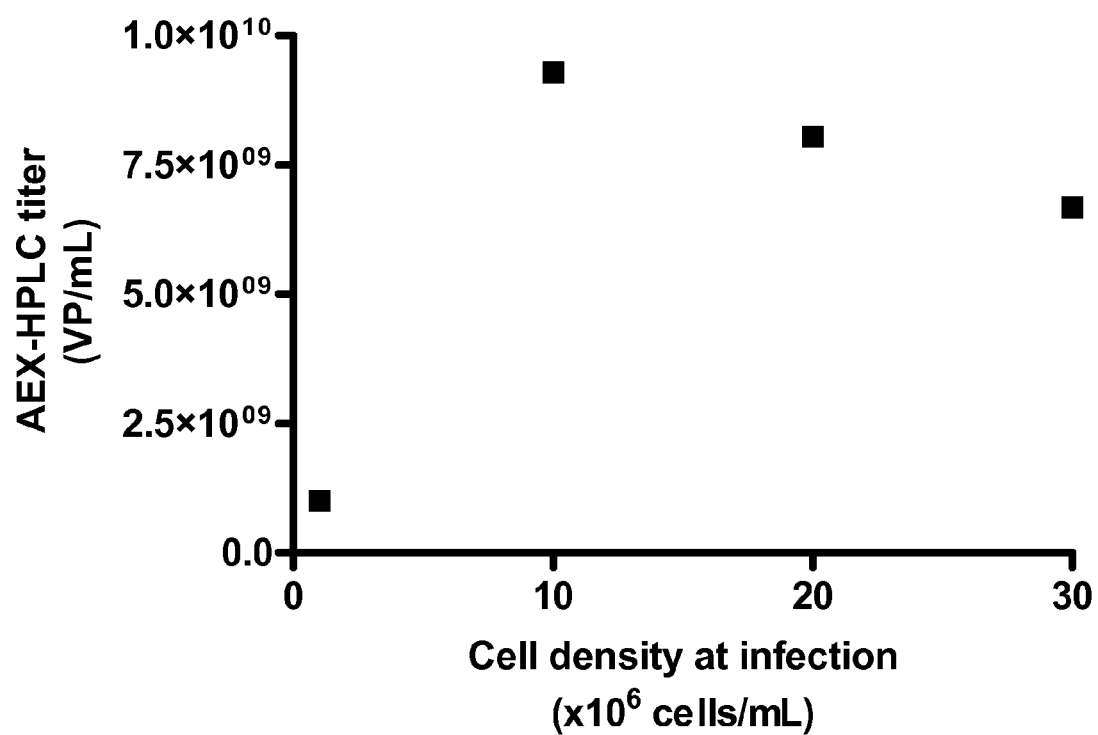
FIG. 1. Infection at high-cell density in shakers with rAd5.

Described herein is a new process for the production of large quantities of recombinant adenovirus 35. This optimized process relies on the ability to infect cultures at high-cell density with preservation of a high-virus productivity per cell. Herewith, it offers a method to obtain a harvested virus solution with high-virus concentration in a single bioreactor. Typical yields of current processes for rAd35 are about $2-3\times10^{11}$ VP/mL. Indeed, it is believed that very large quantities of rAd35 particles can be produced using the processes of the present invention, for instance quantities of at least about $5\times10^{11}$ VP/mL, preferably at least about 6, 7, 8, or $9\times10^{11}$ VP/mL. Preferably at least $1\times10^{12}$ VP/mL of rAd35 are produced, more preferably at least $1.5\times10^{12}$ VP/mL, still more preferably at least $2\times10^{12}$ VP/mL, e.g., between about $1\times10^{12}$ and $5\times10^{12}$ VP/mL. Typically, the process will not yield more than about $1\times10^{13}$ VP/mL of rAd35. The yields that can be obtained with the processes according to the present invention are likely sufficient to prepare the desired amount of certain rAd35 based vaccines in the world, without requiring bioreactor facilities with working volumes larger than 1000 L.

Provided is a method for producing recombinant adenovirus serotype 35 (rAd35), the method comprising: a) culturing producer cells in suspension with a perfusion system; b) infecting the cells at a density of at least $10\times10^6$ viable cells/mL with rAd35; c) further culturing the infected cells with a perfusion system to propagate the rAd35; and d) harvesting the rAd35.

In certain embodiments, the cells in step b) are infected with rAd35 at a density of between about $10\times10^6$ and $50\times10^6$ viable cells/mL. In further embodiments, the cells in step b) are infected with rAd35 at a density of between about $10\times10^6$ and $20\times10^6$ viable cells/mL. In yet further advantageous embodiments, the cells in step b) are infected with rAd35 at a density of between about $10\times10^6$ and $16\times10^6$ viable cells/mL, for instance at about 10, 11, 12, 13, 14 or $15\times10^6$ viable cells/mL.

In other embodiments, the cells in step b) are infected with rAd35 at a density of between about $20\times10^6$ and $50\times10^6$ viable cells/mL.

Producer Cells and Recombinant Adenovirus

A producer cell (sometimes also referred to in the art and herein as a 'packaging cell' or 'complementing cell' or 'host cell') according to the present invention can be any producer cell wherein a desired adenovirus can be propagated. For example, the propagation of recombinant adenovirus vectors is performed in producer cells that complement deficiencies in the adenovirus. Such producer cells preferably have in their genome at least an adenovirus E1 sequence, and thereby are capable of complementing recombinant adenoviruses with a deletion in the E1 region. Further the adenovirus may have a deletion in the E3 region, which is dispensable from the Ad genome, and hence such a deletion does not have to be complemented. Any E1-complementing producer cell can be used, such as human retina cells immortalized by E1, e.g., 911 or PER.C6® cells (see U.S. Pat. No. 5,994,128), E1-transformed amniocytes (See EP Patent 1230354), E1-transformed A549 cells (see, e.g., WO 98/39411, U.S. Pat. No. 5,891,690), GH329:HeLa (Gao et al., 2000, Human Gene Therapy 11: 213-219), 293, and the like. In certain embodiments, the producer cells are, for instance, HEK293 cells, or PER.C6® cells, or 911 cells, or IT293SF cells, and the like. Preferably PER.C6® cells (ECACC deposit 96022940; see U.S. Pat. No. 5,994,128), or cells derived therefrom are used as producer cells.

It is shown herein that recombinant adenovirus serotype 35 (rAd35) has hitherto unknown, advantageous, properties compared to rAd5 in processes applying high-cell density infection. We now also know that yet another serotype again behaves differently in similar processes, suggesting that optimal conditions for large scale production of recombinant adenovirus may have to be established for different serotypes. Hence in certain preferred embodiments, the adenovirus of the invention is rAd35.

Preferably, the adenoviral vector is deficient in at least one essential gene function of the E1 region, e.g., the E1a region and/or the E1b region, of the adenoviral genome that is required for viral replication. In certain embodiments, the vector is deficient in at least one essential gene function of the E1 region and at least part of the nonessential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors deleted of the entire E4 region can elicit lower host immune responses. Examples of suitable adenoviral vectors include adenoviral vectors that lack (a) all or part of the E1 region and all or part of the E2 region, (b) all or part of the E1 region, all or part of the E2 region, and all or part of the E3 region, (c) all or part of the E1 region, all or part of the E2 region, all or part of the E3 region, and all or part of the E4 region, (d) at least part of the E1a region, at least part of the E1b region, at least part of the E2a region, and at least part of the E3 region, (e) at least part of the E1 region, at least part of the E3 region, and at least part of the E4 region, and (f) all essential adenoviral gene products (e.g., adenoviral amplicons comprising ITRs and the packaging signal only). As known to the skilled person, in case of deletions of essential regions from the adenovirus genome, the functions encoded by these regions have to be provided in trans, preferably by the producer cell, i.e., when parts or whole of E1, E2 and/or E4 regions are deleted from the adenovirus, these have to be present in the producer cell, for instance integrated in the genome, or in the form of so-called helper adenovirus or helper plasmids.

The replication-deficient adenoviral vector can be generated by using any species, strain, subtype, or mixture of species, strains, or subtypes, of an adenovirus or a chimeric adenovirus as the source of vector DNA (see, for instance, WO 96/26281, and WO 00/03029), which for instance may provide the adenoviral vector with the capability of infecting certain desired cell types.

In a preferred embodiment of the present invention, rAd35 is used as an adenovirus.

In further embodiments, the adenovirus of the invention lacks at least a portion of the E1-region, e.g., E1A and/or E1B coding sequences, and further comprises heterologous nucleic acid. Suitable heterologous nucleic acid is well-known to the skilled person, and for instance may include transgene open reading frames, for instance open reading frames coding for polypeptides against which an immune response is desired when the rAd vector is used for vaccination purposes, e.g., transgenes suitable to generate an immune response against malaria (see, e.g., WO 2004/055187), HIV, tuberculosis (see, e.g., WO 2006/053871), certain viruses, etc, all well-known to the skilled person. In fact, the nature of the heterologous nucleic acid is not critical to the instant invention, may be any heterologous nucleic acid, and hence needs no further elaboration here.

The person skilled in the art will be aware of the possibilities to propagate adenoviral vectors of different serotypes on specific host cells, using methods such as for instance disclosed in U.S. Pat. No. 6,492,169 or in WO 03/104467, and references therein. For instance, for propagation of E1-deficient rAd35, specific producer cells that express E1B-55K of Ad35 can be constructed, for instance based on existing producer cells that express E1A and E1B of Ad5 such as PER.C6® or HEK293 cells (see, e.g., U.S. Pat. No. 6,492,169), as is known to the skilled person. Alternatively and preferably, existing (Ad5-) complementing cell lines such as for instance PER.C6® or HEK293 can be used without modification of the cells for propagation of E1-deficient rAd35, by inclusion of the E4-orf6 coding sequence of Ad5 into the rAd35 vector, as extensively disclosed in for instance WO 03/104467, incorporated in its entirety by reference herein. Thus, propagation of adenoviral vectors of any serotype can be done on producer cells using means and methods well-known to the person skilled in the art. Adenoviral vectors, methods for construction thereof and methods for propagating thereof, are well-known in the art and are described in, for example, U.S. Pat. Nos. 5,559,099, 5,837, 511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in Virology, B. N. Fields et al., eds., 3d ed., Raven Press, Ltd., New York (1996), and other references mentioned herein.

The construction of adenoviral vectors is well understood in the art and involves the use of standard molecular biological techniques, such as those described in, for example, Sambrook et al., Molecular Cloning, a Laboratory Manual, 2d ed., Cold Spring Harbor Press, Cold Spring Harbor, N.Y. (1989), Watson et al., Recombinant DNA, 2d ed., Scientific American Books (1992), and Ausubel et al., Current Protocols in Molecular Biology, Wiley Interscience Publishers, NY (1995), and other references mentioned herein.

Producer cells according to the invention are cultured to increase cell and virus numbers and/or virus titers. Culturing a cell is done to enable it to metabolize, and/or grow and/or divide and/or produce virus of interest according to the invention. This can be accomplished by methods as such well-known to persons skilled in the art, and includes but is not limited to providing nutrients for the cell, for instance in the appropriate culture media. Different culture media can be used, and choosing the optimal culture medium for the cells and circumstances used is part of the routine tasks of the skilled person in this field. Suitable culture media for the purpose of the present invention are thus well-known to the skilled person and can generally be obtained from commercial sources in large quantities, or custom-made according to standard protocols. Culturing can be done for instance in dishes, roller bottles or in bioreactors, using batch, fed-batch, continuous systems and the like. In order to achieve large scale (continuous) production of virus through cell culture it is preferred in the art to have cells capable of growing in suspension, and it is preferred to have cells capable of being cultured in the absence of animal- or human-derived serum or animal- or human-derived serum components. Suitable conditions for culturing cells are known (see, e.g., Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Cell Culture System and Perfusion System

Bioreactors have been widely used for the large-scale production of biological products from suspension dependent animal cell cultures. According to the invention, the bioreactors used for adenovirus propagation can for instance be stirred tanks, disposable bioreactors, airlift reactors and the like.

According to certain embodiments of the present invention the bioreactor is a stirred tank.

According to certain embodiments of the invention, the bioreactor has a working volume between about 2 L and 2000 L, between meaning herein to include the upper and lower limit values disclosed, i.e., 2 L being the smallest working volume and 2000 L being the largest working volume. Bioreactors having a working volume of any individual value in between these values are meant to be included in the invention. The term "about" for numerical values as used in the present disclosure means the value ±10%. In certain preferred embodiments, the working volume is between 10 L and 1000 L, preferably between 20 L and 800 L, e.g., between 30 L and 600 L, e.g., between 50 L and 500 L, e.g., about 250 L or about 500 L. An advantage of using bioreactors with a working volume according to the invention is that the use of very large volume bioreactors, i.e., those with a working volume of much more than 2000 L, preferably 1000 L, is avoided, and thus the huge capital and time investment in building such a very large bioreactor is not required. Further, the product, i.e., the rAd, is much more concentrated when use is made of the methods of the present invention, which saves time and costs in harvesting and/or further downstream processing of rAd from the bioreactors. The working volume is the effective culture volume in the bioreactor. The stirred tanks generally have a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts. Instrumentation and controls of the bioreactors include (without limitation): agitation, temperature, dissolved oxygen, pH and biomass controls. The agitation, pH, temperature, dissolved oxygen concentration of the cell culture medium are in principle not critical and depend on the type of cell chosen. Preferably, the agitation, pH, temperature, dissolved oxygen concentration are chosen such that it is optimal for the growth of the cells. The person skilled in the art knows how to find the optimal agitation, pH, temperature, dissolved oxygen concentration for the culturing. Usually, the optimal agitation is between 50 and 300 rpm, e.g., 100-250 rpm, the optimal pH is between 6.7 and 7.7, the optimal temperature between 30 and 39° C., e.g., 34, 35, 36, 37 or 38° C.

Most large-scale suspension cultures are operated as batch or fed-batch processes because they are the most straight-forward to operate and scale up. However, continuous processes based on perfusion principles are becoming more common. According to the present invention the producer cells are cultured in a perfusion system. Perfusion culturing of cells has its conventional meaning in the art, i.e., it means that during culturing cells are retained by a separation device in which there is an outflow of liquid having a lower cell density than prior to separation and in which there is an inflow of cell culture medium. The use of perfused culture is in response to the challenge of growing cells at high densities (e.g., $10-50 \times 10^6$ viable cells/mL). In order to increase densities beyond $2-4 \times 10^6$ viable cells/mL, the medium is constantly, or intermittently, replaced with a fresh supply in order to make up for nutritional deficiencies and to remove toxic products. Perfusion also allows for a far better control of the culture environment (pH, $dO_2$, nutrient levels, etc.). Perfusion of fresh medium through the culture can be achieved by retaining the cells with a variety of separation devices (e.g., fine mesh spin filter, hollow fiber or flat plate membrane filters, settling tubes). In preferred embodiments of the process of the present invention, the separation device is a filter module comprising hollow fibers.

With the term "hollow fiber" is meant a tubular membrane. The internal diameter of the tube is preferably between 0.3 mm and 6.0 mm, more preferably between 0.5 mm and 3.0 mm, most preferably between 0.5 mm and 2.0 mm. In certain embodiments, the mesh size (pore size) in the membrane is chosen such that the size of the pores in the mesh is close to the diameter of the cells, ensuring a high retention of cells while cell debris can pass the filter. In other embodiments, the mesh size is significantly smaller than the diameter of the cells. Preferably, the mesh size is between 0.1 µm to 30 µm, e.g., between 0.1 µm and 3 µm, e.g., about 0.2 µm. Filter modules comprising hollow fibers are commercially available from for example General Electric (formerly Amersham). Significant amounts of adenovirus particles were not observed in the outflow culture medium during the process of the present invention, despite the virus particles being smaller than the applied mesh size.

Perfusion is used in order to maintain desired levels of certain metabolites and to remove and thereby reduce impurities in the culture medium. Perfusion rates can be measured in various manners, such as in terms of replacement volumes/unit time or in terms of levels of certain metabolites, which must be maintained, during periods of perfusion. It is typically the case that perfusion is not carried out at all times during culturing and is generally carried out only from time to time during culturing as desired. For example, perfusion is not typically initiated until after certain media components such as glucose begin to become exhausted and need to be replaced.

Several perfusion systems are known in the art and are in principle suitable for the methods of the present invention. With the term "perfusion system" is meant the combination of a bioreactor connected to a separation device. The separation device can either be incorporated in the bioreactor (e.g., fine mesh spin filter) or remain outside the bioreactor (e.g., hollow fiber). In both cases, as explained above, the separation device prevents washout of the cell mass from the reactor and enables medium refreshment.

The present inventors performed pilot experiments with several perfusion systems from which the Alternating Tangential Flow (ATF) perfusion system gave the best results. Therefore, in a preferred embodiment of the invention, the bioreactors are operated with (connected to) an ATF perfusion system (e.g., ATF System, Refine Technology, Co., East Hanover, N.J.). The system consists of a diaphragm pump mounted to one end of a hollow fiber housing. The other end of the housing is attached to a joint assembly, which, in turn, is connected to a bioreactor through an available port. The diaphragm pump and control system serve to generate Alternating Tangential Flow through the hollow fibers. This means that there is one flow in the same direction as (i.e., tangential to) the membrane surfaces of the hollow fibers, which flow is going back and forth, and that there is another flow in a direction substantially perpendicular to the filter surface. Tangential flow can be achieved according to methods known to the person skilled in the art and as described in, for example, in U.S. Pat. No. 6,544,424.

Operation of the ATF perfusion system has been described (Furey, 2002). ATF systems allow the cells to be cultured for a longer period of time and to reach high-cell densities without having a blocked filter. Indeed, extremely high-cell densities of over $100 \times 10^6$ viable cells/mL can be obtained with the use of an ATF perfusion system, e.g., with PER.C6® cells (see, e.g., Yallop et al.). However, in earlier reports the PER.C6® cells in perfusion systems were used for a completely different purpose and not infected with adenovirus.

An additional advantage of the ATF system is that the system generates low-shear stress. Energy is added to the surface of the liquid, generating a low-shear laminar flow. This may be an advantage especially for the present invention, where cells are infected with adenovirus. During perfusion processes, post infection, with the ATF system no loss in cell density was found and no premature cell loss was observed, but rather even cell growth was observed. Since cells remain intact, optimal conditions are created for virus propagation.

The perfusion with the ATF system is therefore advantageous during the preculture phase (step a according to the present invention), since it allows obtaining very high-cell densities, and the cells are in good condition for subsequent infection with adenovirus, possibly contributing to the high yields obtained. In order to reach the high-cell densities, the culture medium is in certain embodiments at least partially perfused during a portion of time during cell growth of the producer cells (step a). In certain embodiments, perfusion is started once a cell density between about $2 \times 10^6$ viable cells/mL and $8 \times 10^6$ viable cells/mL is reached.

Further, the perfusion with the ATF system is advantageous after the infection stage (step c according to the present invention), since it allows obtaining very high adenovirus yields from the infected cells. In preferred embodiments therefore, both the preculture stage and the post-infection stage of the processes of the invention employ an ATF perfusion system. The volume of culture medium used during ATF can be varied according to needs of the cells as can easily be established and adjusted by the skilled person, and typically varies between 0.5-5 vessel volumes/day (vol/d), e.g., between 1-3 vol/d, e.g., about 2 vol/d. In certain advantageous embodiments, the refreshment rate is between about 1 and 2 vol/d, as the inventors have shown herein that this gives very good results in terms of yields and quality of the rAd35 obtained, while at the same time medium consumption and therefore costs associated therewith are still reasonable.

Finally the ATF perfusion system is a scalable system. Different size ATF units are available. Since airflow is used to drive the culture through the hollow fiber membrane, one can generate very rapid, low-shear tangential flow rates enabling the technology to be used from R&D to production scale up to 1000 L (Furey, 2002). Possibly, further developments will allow even further upscaling of the ATF perfusion system.

In Yuk et al., rAd5 is produced using a tumor cell line, and therein the complete process is performed in a single bioreactor, which will take about 8-10 days in a production bioreactor. In certain embodiments of the present invention, two different bioreactors are used, one for the preculture (step a; preculture bioreactor), and one for the infection (step b) and post-infection culture (step c; production bioreactor) of the cells. An advantage of the use of two separate bioreactors for these steps is that only about 1.5-5, typically about 2-3 days of culturing in the production bioreactor are required, and therefore much more runs can be performed per year. Addition of a large amount of fresh culture medium during infection is further advantageous for reducing the volume of culture medium required during perfusion in the production bioreactor. In alternative embodiments it is also possible to perform all steps a-c of the invention in a single bioreactor.

Infection

In the methods of the invention, producer cells are infected with recombinant adenovirus. Typically, the virus will be exposed to the appropriate producer cell under optimal conditions, permitting uptake of the virus. The optimal conditions depend on the type of cell and on the type of adenovirus chosen. The person skilled in the art knows how to find the optimal conditions, i.e., for agitation, pH, temperature, dissolved oxygen ($dO_2$ or DO), Multiplicity of infection (MOI). Usually, the optimal agitation is between about 50 rpm and 300 rpm, typically about 100-200, e.g., about 150, typical DO is 20-60%, e.g., 40%, the optimal pH is between 6.7 and 7.7, the optimal temperature between 30° C. and 39° C., e.g., 34-37° C., and the optimal MOI between 5 and 1000, e.g., about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art.

In a certain embodiment of the present invention, perfusion is stopped prior to infection and is resumed after between 1 and 20 hours, e.g., 3-15 hours, e.g., 5 hours post infection. This delay should allow virus particles to enter the cells and prevent the virus particles from being flushed out of the system. Perfusion rates, post infection, are defined in terms of the glucose level that is maintained by means of the perfusion. For example, in the present invention the glucose concentration in the medium is usually maintained at a concentration of between about 2 mmol/L and 20 mmol/L, typically between about 5 and 10 mmol/L.

It was advantageously possible to infect a bioreactor with rAd35 at high-cell densities, i.e., higher than $10\times10^6$ viable cells/mL, with preservation of high-virus productivity per cell. In certain embodiments, the specific productivity remains between about $0.5\times10^5$ and $1.5\times10^5$ VP/cell.

Moreover, in the present invention, the viability of the cell culture prior to infection remains higher than 75%. Meaning that at least 75% of the total amount of cells in the culture is viable at the moment of infection. In certain embodiments, the viability of the cell culture at infection is at least 80%, in further embodiments at least 85%. Viability can be measured using routine methods available to the skilled person, e.g., trypan blue exclusion, Casy cell count, and the like.

In a certain embodiment, the cell density at infection is between about $10\times10^6$ and $50\times10^6$ viable cells/mL, e.g., between about $10\times10^6$ and $20\times10^6$ viable cells/mL, e.g., between about $10\times10^6$ and $15\times10^6$ viable cells/mL, e.g., between about $10\times10^6$ and 14 viable cells/mL, e.g., about $12\text{--}13\times10^6$ viable cells/mL. These cell densities allow for high-virus productivity with limited accumulation of cell debris and host cell DNA, which gives an advantage of these embodiments in downstream processing of the adenovirus harvest. Thus, the present invention provides an optimized process for rAd35 production, yielding high numbers of rAd35 particles of good quality, while at the same time providing a harvest material that is still manageable for downstream processing purposes.

In other embodiments disclosed herein, the cell density at infection is between about $15\times10^6$ and $50\times10^6$ viable cells/mL, e.g., between about $17\times10^6$ and $45\times10^6$ viable cells/mL, e.g., between about $20\times10^6$ and $40\times10^6$, e.g., between $25\times10^6$ and $35\times10^6$ viable cells/mL, e.g., about $30\times10^6$ viable cells/mL. Infections at these cell densities may produce even higher concentrations of recombinant adenovirus, in particular rAd35, and surpass the yields for rAd35 disclosed thus far. As shown for the first time in the present disclosure, in contrast to rAd5 infection at high-cell densities (above $10\times10^6$ viable cells/mL), infection with rAd35 at densities above $10\times10^6$ viable cells/mL still increased the volumetric productivity of rAd35 with increasing cell densities up to at least $30\times10^6$ viable cells/mL at infection, using producer cells in suspension with a perfusion system.

In a preferred embodiment of the invention, a method is provided for producing at least $1\times10^{12}$ rAd35 virus particles (VP)/mL.

The processes of the current invention allow the recovery of rAd35 with a physical particle to infectious particle ratio of less than 30:1, which is an important parameter for adenovirus that is to be administered to humans. This can be measured as a virus particle (VP)/infectious unit (IU) ratio, for instance employing a QPA assay (Wang et al., 2005). A lower ratio is advantageous since less virus particles need to be administered to infect the same number of cells in such a case. Current FDA regulations require a VP/IU ratio of less than 30:1, and hence the processes of the invention described herein are suitable to prepare large numbers of rAd35 that fulfill this particular requirement. The authors of Yuk et al., 2004 reported lower absolute numbers of virus particles than the numbers disclosed herein, and further the VP/IU ratio of the samples disclosed in Yuk et al., 2004 are around 100 (FIG. 2A and 2B in Yuk et al., 2004). In contrast, we report higher absolute yields and moreover significantly better VP/IU ratios of below 20:1. In certain preferred embodiments therefore, the processes of the invention provide batches of rAd35 that have a VP/IU ratio of less than 20:1, e.g., between about 20:1 and about 5:1.

Methods of Cell Harvest and Lysis

After infection of an adenovirus, the virus replicates inside the cell and is thereby amplified. Adenovirus infection results finally in the lysis of the cells being infected. The lytic characteristics of adenovirus, therefore, permits two different modes of virus production. The first mode is harvesting virus prior to cell lysis, employing external factors to lyse the cells. The second mode is harvesting virus supernatant after (almost) complete cell lysis by the produced virus (see, e.g., U.S. Pat. No. 6,485,958, describing the harvesting of adenovirus without lysis of the host cells by an external factor). For the latter mode, longer incubation times are required in order to achieve complete cell lysis, and hence high yields of virus. Furthermore, the gradual spill of the host cell contents into the medium may be detrimental to the integrity and yield of the obtained viruses. Hence, it is preferred to employ external factors to actively lyse the cells for harvesting the adenovirus, according to the invention.

Methods that can be used for active cell lysis are known to the person skilled in the art, and have for instance been discussed in WO 98/22588, p. 28-35. Useful methods in this respect are, for example, freeze-thaw, solid shear, hypertonic and/or hypotonic lysis, liquid shear, sonication, high-pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are, for instance, discussed in WO 98/22588, p. 29-33. Detergents, as used herein, can include anionic, cationic, zwitterionic, and nonionic detergents. It is clear to the person skilled in the art that the concentration of the detergent may be varied, for instance, within the range of about 0.1%-5% (w/w). In one embodiment, the detergent used is Triton X-100.

Nuclease may be employed to remove contaminating, i.e., mostly producer cell, nucleic acids. Exemplary nucleases suitable for use in the present invention include BENZONASE®, PULMOZYME®, or any other DNase and/or RNase commonly used within the art. In preferred embodiments, the nuclease is BENZONASE®, which rapidly hydrolyzes nucleic acids by hydrolyzing internal phosphodiester bonds between specific nucleotides, thereby reducing the viscosity of the cell lysate. BENZONASE® can be commercially obtained from Merck KGaA (code W214950). The concentration in which the nuclease is employed is preferably within the range of 1-100 units/mL.

Methods for harvesting adenovirus from cultures of producer cells have been extensively disclosed in WO 2005/080556.

The time of harvest is between about 24 and 120 hours post infection, e.g., between about 48 and 96 hours post infection, e.g., 72 hours post infection.

Methods of Purification

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also, WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Purification may for instance be achieved by density gradient centrifugation, as for instance discussed in WO 98/22588, p. 59-61.

Preferably however, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process.

It is, for instance, possible to purify adenoviruses by anion exchange chromatography steps, see for instance WO 05/080556. For adenovirus purification, it is preferred to use at least one anion exchange chromatography step. After the anion exchange chromatography step, the virus may be sufficiently pure. In certain embodiments, however, a size exclusion chromatography step is further performed to increase the robustness of the process. This step may be prior to or after the anion exchange chromatography step. Other purification steps may also be suitably combined with an anion exchange chromatography step.

The use of anion exchange chromatography for adenovirus purification has been extensively described, and this aspect is therefore well within the reach of the person skilled in the art. Many different chromatography matrices have been employed for purification of adenovirus and are suitable, and the person skilled in the art can easily find the optimal anion exchange material for purifying the virus, for instance guided by the following art.

U.S. Pat. No. 5,837,520 (see also Huyghe et al., 1995, Human Gene Therapy 6: 1403-1416) describes a method of purifying adenovirus wherein the host cell lysate is treated with a nuclease, followed by anion exchange and metal ion affinity chromatography.

U.S. Pat. No. 6,485,958 describes the use of strong anion exchange chromatography for purification of recombinant adenovirus.

Anion exchange chromatography has been employed with fluidized bed columns for the purification of adenovirus particles, see WO 00/50573.

Further, expanded bed anion exchange chromatography, and certain chromatographic resins for anion exchange chromatography for purification of adenovirus particles have been described in U.S. Pat. No. 6,586,226.

In addition to anion exchange columns, anion exchange membrane chromatography products such as those produced by Pall (e.g., Mustang™ series) and Sartorius (e.g., Sartobind series) are suitable. For use of these filters and their advantages in adenovirus purification see for instance WO 03/078592 and WO 2005/080556.

U.S. Pat. No. 6,537,793 describes the purification of adenoviral particles from host cells using ion-exchange chromatography, in particular teaching a preference for Q Sepharose XL types of chromatographic support for this purpose. In one embodiment of the present invention, an adenovirus is further purified using a Q Sepharose XL column.

The purification process may also suitably employ a size exclusion chromatography step.

International application WO 97/08298 describes the purification of adenoviruses using certain chromatographic matrices to prevent damage to the viruses, including anion exchange and size exclusion steps. U.S. Pat. No. 6,261,823 describes a method for purifying adenovirus wherein the adenovirus preparation is subjected to anion exchange chromatography followed by size exclusion chromatography. In the size exclusion step, a group separation of viral particles from impurities of low-molecular weight is achieved.

It is also possible to employ a hydroxyapatite medium for purifying adenovirus, see WO 02/44348.

A reversed-phase adsorption step might also be used, as for instance described in WO 03/097797, p. 26.

International application WO 97/08298 describes the purification of adenoviruses using certain chromatographic matrices to prevent damage to the viruses, including anion exchange and size exclusion steps.

Certain ultrafiltration methods are also very suitable for purification of adenovirus, as disclosed in WO 2006/108707. Such steps may be performed in addition to or instead of certain chromatographic purification steps.

Preparing a Pharmaceutical Preparation

In certain embodiments, the purified adenovirus is formulated into a pharmaceutical composition. This can be done according to a variety of methods and using a variety of buffers all according to routine methods well-known to the person skilled in the art. In general, it entails bringing the adenovirus particles in a pharmaceutically acceptable composition, comprising the adenovirus and at least a pharmaceutically acceptable excipient. Such a composition may be prepared under conditions known to the skilled person, and in certain embodiments is suitable for administration to humans.

For instance the adenovirus may be buffer exchanged during group separation to—and finally stored in—the buffer that is also used for the Adenovirus World Standard (Hoganson et al., Development of a stable adenoviral vector formulation, Bioprocessing March 2002, p. 43-48): 20 mM Tris pH 8, 25 mM NaCl, 2.5% glycerol.

Many other buffers can be used, and several examples of suitable formulations for the storage and pharmaceutical administration of purified (adeno)virus preparations can for instance be found in European Patent No. 0853660, and in International Patent applications WO 99/41416, WO 99/12568, WO 00/29024, WO 01/66137, WO 03/049763.

In certain embodiments, the adenovirus vectors are used as vaccines, and these are typically held in pharmaceutically acceptable carriers or excipients, and/or diluents. Pharmaceutically acceptable carriers or excipients and diluents are well-known in the art and used extensively in a wide range of therapeutic products. Preferably, carriers are applied that work well in vaccines. More preferably, the vaccines further comprise an adjuvant. Adjuvants are known in the art to further increase the immune response to an applied antigenic determinant, and pharmaceutical compositions comprising adenovirus and an aluminum phosphate adjuvant are for instance disclosed in WO 2007/110409.

For administration to humans, the invention may employ pharmaceutical compositions comprising the rAd and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well-known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). The purified rAd preferably is formulated and administered as a sterile solution although it is within the scope of this invention to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The rAd typically is in a solution having a suitable pharmaceutically acceptable buffer, and the solution of rAd may also contain a salt. Optionally, a stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients.

The present invention discloses methods to produce adenoviral vectors, in particular rAd35, with very high yields, and as far as we are aware the yields obtained and disclosed herein have not been reported before. In the processes of the invention, bioreactors are used, and the bioreactor with the very high number of adenovirus particles per volume is a direct (intermediate) product of the invention. The invention therefore also provides a bioreactor with a working volume of between 2 L and 2000 L, preferably between 10 L and 1000 L, comprising: culture medium, producer cells, and at least $1\times10^{12}$ rAd35 virus particles (VP)/mL. The culture medium can be any culture medium suitable for propagation of the cells and infection for adenovirus, as described above. The aspects of the bioreactor volume, the producer cells and the number of rAd35 particles and VP/IU ratio are as described above for the methods of the invention. In preferred embodiments, the bioreactor is connected to an ATF perfusion system.

In yet another aspect, provided is a method for producing at least $1\times10^{12}$ rAd35 virus particles (VP)/mL, the method comprising: a) culturing producer cells in suspension with a perfusion system; b) infecting the cells at a density of between $10\times10^6$ viable cells/mL and $16\times10^6$ viable cells/mL with rAd35; c) further culturing the infected cells with a perfusion system to propagate the rAd35, whereby the concentration of rAd35 virus particles reaches at least $1\times10^{12}$ VP/mL; and d) harvesting the rAd35. Prior to the instant disclosure, it was unknown if such high yields of rAd35 were feasible at all, let alone how to achieve such high yields. The instant invention discloses that these yields are possible according to methods disclosed herein. Preferably, the physical particle to infectious particle ratio of the harvested rAd35 is less than 30:1. Advantageous further embodiments are as described for the methods according to the invention as described supra.

The invention is further explained in the following examples. The examples do not limit the invention in any way. They merely serve to clarify the invention.

EXAMPLES

Example 1: Infection at High-Cell Densities with an Ad5 Vector

From a PER.C6® working cell bank, cells were thawed and propagated in serum free culture medium in a humidified incubator at 37° C. and 10% $CO_2$. Subculture was performed every 3 to 4 days until sufficient cell density was reached to inoculate a 2 L bioreactor at a volume of 1.5 L and a cell density of 0.2 to $0.5\times10^6$ viable cells/mL. Cells were propagated in the bioreactor at 37° C., DO of 40%, and a pH of 7.3. The ATF perfusion process was started at a cell density of $4.7\times10^6$ total cells/mL. The ATF was from Refine Technology, Co., East Hanover, N.J. After 89 hours a cell density was reached of $12.4\times10^6$ total cells/mL. At this moment a part of the cells were harvested and the cells were centrifuged for 5 minutes at 300 g. The cell pellet was re-suspended to the following concentrations in fresh serum free medium:

$1.3\times10^6$ viable cells/mL, 30 mL/shaker, two 250 mL shakers $10\times10^6$ viable cells/mL, 30 mL/shaker, two 250 mL shakers $20\times10^6$ viable cells/mL, 30 mL/shaker, two 250 mL shakers $30\times10^6$ viable cells/mL, 30 mL/shaker, two 250 mL shakers The shakers were infected with Ad5.CS (a rAd5 vector; Shott et al., 2008) at an MOI of 90 VP/cell and incubated at 36° C., 10% $CO_2$ and 100 rpm. Day 1 and 2 post infection medium refreshment was performed for the shakers infected at 10, 20, and $30\times10^6$ viable cells/mL. This medium refreshment was performed by a centrifugation step for 5 minutes at 300 g and re-suspending the cell pellet in 30 mL fresh medium per shaker. Day 3 post infection, the shakers were harvested and sampled for AEX-HPLC analysis. Cell lysis of the harvest was performed by mixing 1 mL sample volume of each shaker with 100 μL 10% Triton X-100 and incubation at 37° C. for 30 minutes. After incubation the samples were mixed with 2.42 μL benzonase/$MgCl_2$ followed by a subsequent incubation step of 30 minutes at 37° C. Finally 100 μL 50% sucrose was added to samples. After a centrifugation step of 5 minutes at 2500 g, the samples were stored below −65° C. until analysis by AEX-HPLC was perfoimed to determine the number of virus particles produced (VP/mL). The results are presented in FIG. 1.

The volumetric yield of an infection at a cell density of $10\times10^6$ viable cells/mL was 10 fold higher than at $1\times10^6$ viable cells/mL. This was somewhat unexpected given the cell density effect reported in earlier reports at much lower densities (i.e., at about $0.5-3\times10^6$ cells/mL, e.g., Maranga et al., 2005; Kamen et al., 2004; Altaras et al., 2005). However, past the $10\times10^6$ cells/mL, a cell density effect was observed and volumetric yields decreased.

Thus, with recombinant Ad5 a cell density effect is seen in the perfusion system.

Example 2: Infection with rAd35 at Low Cell Densities ($1-1.6\times10^6$ Viable Cells/mL)

In Example 1, rAd5 was used. However, different adenovirus serotypes are known and have been described for different purposes. These serotypes may have different properties, and hence processes useful for one serotype are not always necessarily suitable for another serotype. This may especially be relevant in industrial scale processes, where seemingly small differences may be economically of great importance. One particularly advantageous serotype for use in, for instance, vaccines is Ad35, and in the following examples we test the feasibility to improve yields of rAd35 to obtain large quantities thereof. This example shows infection with a rAd35 vector at low-cell densities, as a comparison to the following examples where cells are infected at higher-cell densities.

From a PER.C6® working cell bank, cells were thawed and propagated in serum-free culture medium in a humidified incubator at 37° C. and 10% $CO_2$. Subculture was performed every 3 to 4 days until sufficient cell density was reached to inoculate 10 L bioreactors at a volume of 5 L and a cell density of 0.2 to $0.35 \times 10^6$ viable cells/mL. Cells were propagated in the bioreactor at 37° C., DO of 40%, and a pH of 7.3. Four days after inoculation (when a cell density was reached between 2 to $3.5 \times 10^6$ viable cells/mL) the cell suspension was diluted with 5 L fresh medium and subsequently infected with rAd35.TB-S (a rAd35 vector; Radosevic et al., 2007) at an MOI of 70 VP/cell. Virus propagation was performed at 36° C., pH 7.3 and DO 40%. Three days after infection the bioreactors were sampled for cell count and virus production determination. To release the virus, 1 mL sample of each bioreactor was mixed with 100 μL 10% Triton X-100 and incubated at 37° C. for 30 minutes. After incubation the samples were mixed with 2.42 μL benzonase/$MgCl_2$ followed by a subsequent incubation step of 30 minutes at 37° C. Finally, 100 μL 50% sucrose was added to the samples. After a centrifugation step of 5 minutes at 2500 g, the samples were stored at a temperature below −65° C. until analysis by AEX-HPLC. A total of ten bioreactor runs were performed and analyzed according to above described process, and these runs gave consistent results (not shown). The average virus particle production was $2.3 \times 10^{11}$ VP/mL.

For a yearly demand of about $1.5 \times 10^{19}$ VP, with such a yield about 65000 L would have to be processed. This would require large facilities and therefore large upfront investment during vaccine development.

Example 3: Feasibility Study of an Infection Process of rAd35 at High-Cell Densities (>$10 \times 10^6$ Viable Cells/mL)

From a PER.C6® working cell bank, cells were thawed and propagated in serum-free culture medium in a humidified incubator at 37° C. and 10% $CO_2$. Subculture was performed every 3 to 4 days until sufficient cell density was reached to inoculate a 2 L bioreactor at a volume of 1.5 L and a cell density of 0.2 to $0.5 \times 10^6$ viable cells/mL. Cells were propagated in the bioreactor at 37° C., DO of 40%, and a pH of 7.3. Medium perfusion was started at a cell density of $6.8 \times 10^6$ total cells/mL, using an ATF system. After 70 hours, a cell density was reached of $36.8 \times 10^6$ total cells/mL. At this moment, the following infections were performed:

Infection in shakers at cell densities of:
  $1.3 \times 10^6$ viable cells/mL, 30 mL/shaker, two 250 mL shakers
  $10 \times 10^6$ viable cells/mL, 30 mL/shaker, two 250 mL shakers
  $20 \times 10^6$ viable cells/mL, 30 mL/shaker, two 250 mL shakers
  $30 \times 10^6$ viable cells/mL, 30 mL/shaker, two 250 mL shakers
Infection at 2 L bioreactor scale at $8.7 \times 10^6$ total cells/mL (84% viability)

One hour after infection of the bioreactor, a sample was withdrawn from the bioreactor and transferred to two 250 mL shakers, 30 mL/shaker For the infection process in 250 mL shakers, a part of the cell suspension from the 2 L bioreactor was harvested and this suspension was centrifuged for 5 minutes at 300 g. The cell pellet was re-suspended to the above-mentioned concentrations in fresh serum-free medium. The shakers were infected with Ad35.TB-S at an MOI of 70 VP/cell and incubated at 36° C., 10% $CO_2$ and 100 rpm. Day 1 and 2 post infection medium refreshment was performed for the shakers infected at 10, 20, and $30 \times 10^6$ viable cells/mL. This medium refreshment was performed by a centrifugation step for 5 minutes at 300 g and re-suspending the cell pellet in 30 mL fresh medium per shaker. Day 3 post infection the shakers were harvested and sampled for AEX-HPLC analysis. Cell lyses of the harvest was performed by mixing 1 mL sample volume of each shaker with 100 μL 10% Triton X-100 and incubation at 37° C. for 30 minutes. After incubation, the samples were mixed with 2.42 μL benzonase/$MgCl_2$ followed by a subsequent incubation step of 30 minutes at 37° C. Finally 100 μL 50% sucrose was added to samples. After a centrifugation step of 5 minutes at 2500 g, the samples were stored below −65° C. until analysis by AEX-HPLC was performed.

The remaining cells in the 2 L bioreactor were diluted with fresh serum-free medium to a cell concentration of $8.7 \times 10^6$ total cells/mL (84% viability). The bioreactor was infected with Ad35.TB-S at an MOI of 70 VP/cell and incubated at 36° C., pH 7.3 and DO of 40%. The ATF system was started 15 hours after infection at a medium refreshment rate of 1 bioreactor volume per day. Day 1, 2, 3, and 4 post infection the bioreactor was sampled for cell count (CASY cell counter) and virus production determination by AEX-HPLC. Sample preparation was performed as described above. The samples were stored below −65° C. until analysis by AEX-HPLC was performed.

Approximately one hour after infection of the bioreactor a sample of at least 60 mL was taken from the 2 L bioreactor and two infections (in 250 mL shakers) were started at a volume of 30 mL per shaker. Day 1 and 2 post infection medium refreshment was performed to mimic the perfusion system. This medium refreshment was performed by a centrifugation step for 5 minutes at 300 g and re-suspending the cell pellet in 30 mL fresh medium per shaker. Day 3 post infection the shakers were harvested and sampled for AEX-HPLC analysis. Sample preparation was performed as described above. The samples were stored below −65° C. until analysis by AEX-HPLC was performed.

Figure 2:
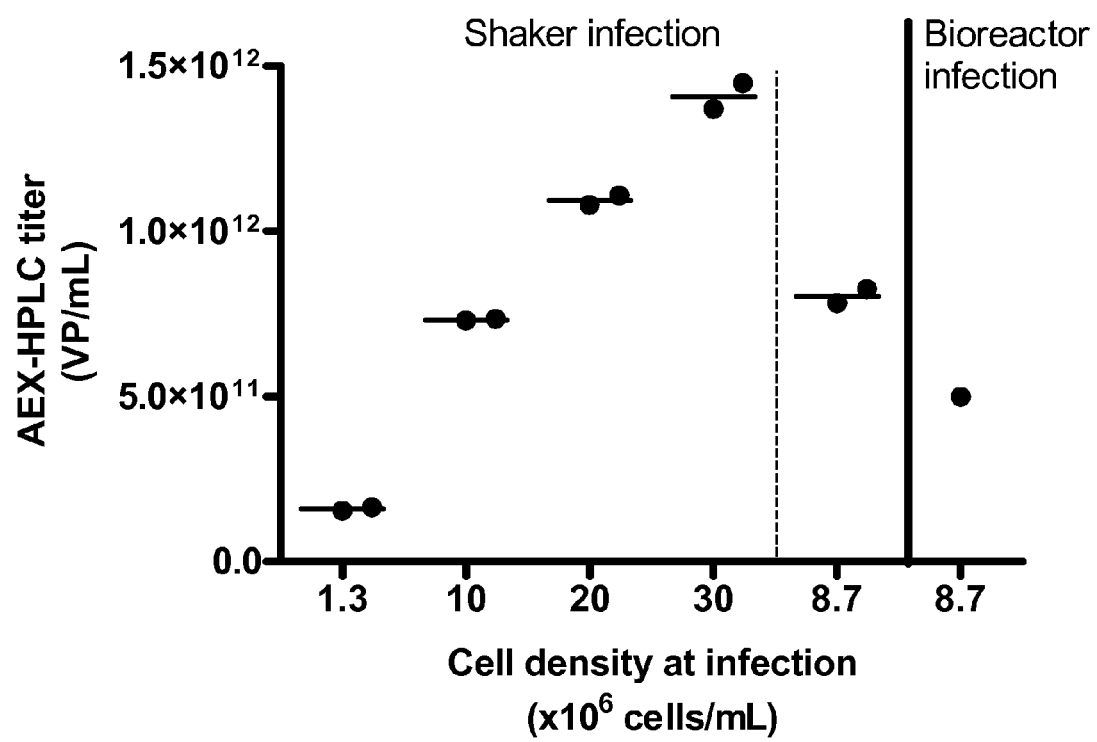
FIG. 2. Infection at high-cell density in shakers and 2 L bioreactor with rAd35.TB-S.

Results are presented in FIG. 2. Results show that infection between $1.3 \times 10^6$ viable cells/mL and $30 \times 10^6$ viable cells/mL is possible. In contrast to the results with rAd5, the total yields of rAd35 increased with increasing cell density at infection even above the $10 \times 10^6$ viable cells/mL samples. At $30 \times 10^6$ viable cells/mL a volumetric yield of $1.4 \times 10^{12}$ VP/mL was reached.

The results clearly indicate that infections with Ad35.TB-S at high-cell densities, i.e., $10 \times 10^6$ viable cells/mL or higher, are possible. Even at $30 \times 10^6$ viable cells/mL, infections gave high-volumetric yields.

It is noted that a decrease is seen in unit productivity from 120.000 VP/cell at $1.3 \times 10^6$ cells to 47.000 VP/cell at $30 \times 10^6$ viable cells/mL. The shakers started from a cell suspension, which was infected in the bioreactor, show a harvest yield of $8.0 \times 10^{11}$ VP/mL and a unit productivity of 92.000 VP/cell. The results in the 2 L bioreactor are somewhat lower: a harvest yield is reached of $5 \times 10^{11}$ VP/mL, which is a unit productivity of 57.000 VP/cell.

Figure 3:
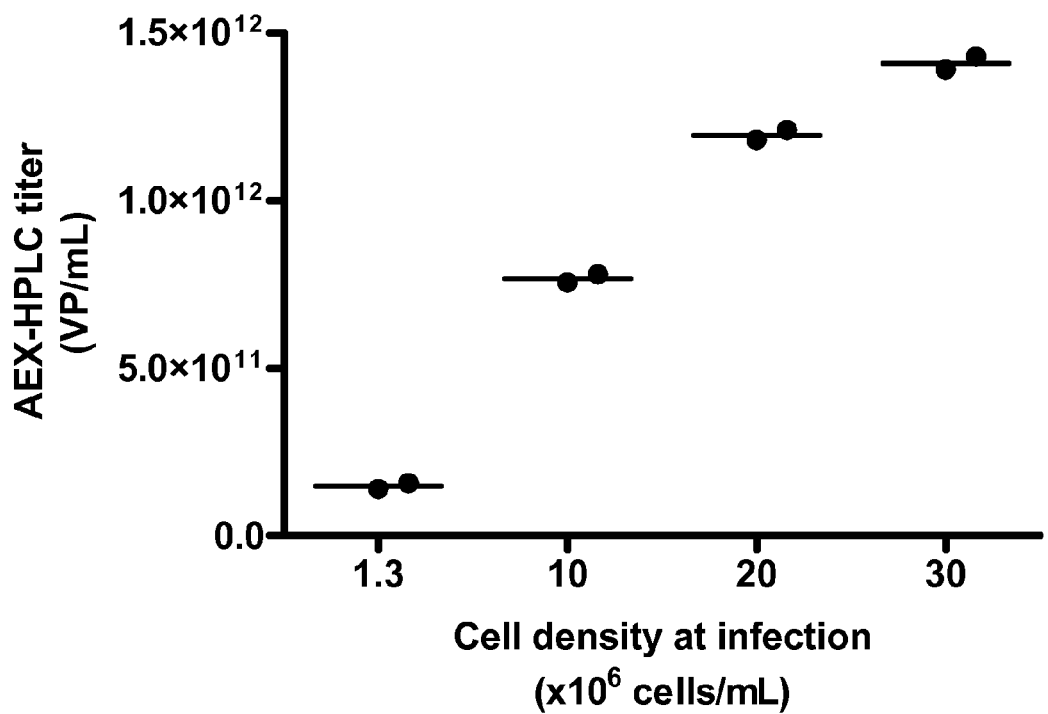
FIG. 3. Infection at high-cell density in shakers with rAd35.eGFP.

Example 4: Feasibility of Infection at High-Cell Densities with Another rAd35 Vector From a PER.C6® working cell bank, cells were thawed and propagated in serum-free culture medium in a humidified incubator at 37° C. and 10% $CO_2$. Subculture was performed every 3 to 4 days until sufficient cell density was reached to inoculate a 2 L bioreactor at a volume of 1.5 L and a cell density of 0.2 to $0.5 \times 10^6$ viable cells/mL. Cells were propagated in the bioreactor at 37° C., DO of 40%, and a pH of 7.3. The ATF perfusion process was started at a cell density of $5.1 \times 10^6$ total cells/mL. After 70 hours a cell density was reached of $25 \times 10^6$ total cells/mL. At this moment a part of the cells were harvested. The cells were centrifuged for 5 minutes at 300 g and the cell pellet was re-suspended to the following concentrations in fresh serum-free medium:

- $1.3 \times 10^6$ viable cells/mL, 30 mL/shaker, two 250 mL shakers
- $10 \times 10^6$ viable cells/mL, 30 mL/shaker, two 250 mL shakers
- $20 \times 10^6$ viable cells/mL, 30 mL/shaker, two 250 mL shakers
- $30 \times 10^6$ viable cells/mL, 30 mL/shaker, two 250 mL shakers The shakers were infected with Ad35.eGFP (rAd35 comprising another transgene, viz. a GFP gene) at an MOI of 70 VP/cell and incubated at 36° C., 10% $CO_2$ and 100 rpm. Day 1 and 2 post infection medium refreshment was performed for the shakers infected at 10, 20, and $30 \times 10^6$ viable cells/mL. This medium refreshment was performed by a centrifugation step for 5 minutes at 300 g and re-suspending the cell pellet in 30 mL fresh medium per shaker. Day 3 post infection, the shakers were harvested and sampled for AEX-HPLC analysis. Cell lysis of the harvest was performed by mixing 1 mL sample volume of each shaker with 100 µL 10% Triton X-100 and incubation at 37° C. for 30 minutes. After incubation, the samples were mixed with 2.42 µL benzonase/$MgCl_2$ followed by a subsequent incubation step of 30 minutes at 37° C. Finally 100 µL 50% sucrose was added to samples. After a centrifugation step of 5 minutes at 2500 g, the samples were stored below −65° C. until analysis by AEX-HPLC was performed. The results are presented in FIG. 3. The results show that infections at high-cell densities are also feasible with another Ad35 vector (Ad35.eGFP). The volumetric yields (FIG. 3) and unit productivity (data not shown) were in the same range as for the Ad35.TB-S vector.

Example 5: Further Experiments of Infection at High-Cell Densities with a rAd35 Vector From a PER.C6® working cell bank, cells were thawed and propagated in serum-free culture medium in a humidified incubator at 37° C. and 10% $CO_2$. Subculture was performed every 3 to 4 days until sufficient cell density was reached to inoculate a 2 L bioreactor at a cell density of $0.25 \times 10^6$ viable cells/mL. Cells were propagated in the 2 L bioreactor at 37° C., DO of 40%, and a pH of 7.3. When a cell density of approximately $3.7 \times 10^6$ total cells/mL was reached (day 4 post inoculation) an ATF system was started. After 67 hours a cell density of $40.7 \times 10^6$ total cells/mL was reached. At this moment a part of the cell suspension was harvested and the remaining cells were diluted with fresh medium in the 2 L bioreactor to a cell density of $12.7 \times 10^6$ total cells/mL (87% viability, hence $11 \times 10^6$ viable cells/mL). Subsequently the 2 L bioreactor was infected with Ad35.TB-S at an MOI of 70 VP/cell and incubated at 36° C., pH 7.3 and DO of 40%. The ATF system was started 15 hours post infection at a medium refreshment rate of 5 vessel volume per day. On day 1, 2, 3, and 4 post infection the 2 L bioreactor was sampled for cell count and virus production by AEX-HPLC. To release the virus 1 mL sample was mixed with 100 µL 10% Triton X-100 and incubated at 37° C. for 30 minutes. After incubation, the sample was mixed with 2.42 µL benzonase/$MgCl_2$ followed by a subsequent incubation step of 30 minutes at 37° C. Finally 100 µL 50% sucrose was added to the samples. After a centrifugation step of 5 minutes at 2500 g the samples were stored at a temperature below −65° C. until analysis by AEX-HPLC. The results are presented in Table 1.

TABLE 1

Results example 5.

| Day post infection | Cell count ($\times 10^6$ total cells/mL) | AEX-HPLC (VP/mL) | QPA (IU/mL) | AEX/QPA (VP/IU) |
|---|---|---|---|---|
| 0 | 12.70 | NA | NA | NA |
| 1 | 22.18 | Below LOQ | $1.77 \times 10^9$ | — |
| 2 | 9.20 | $1.34 \times 10^{12}$ | $8.5 \times 10^{10}$ | 15.8 |
| 3 | 10.10 | $1.46 \times 10^{12}$ | $8.3 \times 10^{10}$ | 17.6 |
| 4 | 7.60 | $1.43 \times 10^{12}$ | $8.3 \times 10^{10}$ | 17.2 |

The results demonstrated that infections at cell densities above $10 \times 10^6$ viable cells/mL are feasible in bioreactors coupled to a perfusion system and that it is possible to increase the volumetric yield almost 7 times compared to a batch process (Example 2). No premature cell loss of the infected culture was observed, indicating that the ATF process is an appropriate system for culturing infected cells.

An FDA requirement for rAd batches is a ratio of VP/IU<30. QPA (Q-PCR based potency assay; Wang et al., 2005) analysis showed that all samples met this requirement. In contrast, the samples disclosed in Yuk et al., 2004 have a VP/IU ratio of around 100 (FIG. 2A and 2B therein). The physical particles to infectious particles ratio is a relevant parameter for adenoviruses, and a lower ratio is preferred for rAd batches. The batches prepared in this Example consistently have such a low ratio of between about 15:1 to 18:1.

For a yearly demand of about $1.5 \times 10^{19}$ VP and with a yield of about $1.5 \times 10^{12}$ VP/mL, about 10000 L would have to be processed. These volumes can be processed in facilities of 1000 L or less, and would thus reduce the upfront cost commitment during vaccine development.

Example 6: Further Experiments of Infection at High-Cell Densities with a rAd35 Vector with Reduced Perfusion Rates From a PER.C6® working cell bank, cells were thawed and propagated in serum-free culture medium in a humidified incubator at 37° C. and 10% $CO_2$. Subculture was performed every 3 to 4 days until sufficient cell density was reached to inoculate a 2 L bioreactor at a cell density of $0.59 \times 10^6$ viable cells/mL. Cells were propagated in the 2 L bioreactor at 37° C., DO of 40%, and a pH of 7.3. When a cell density of approximately $2.9 \times 10^6$ total cells/mL was reached (day 4 post inoculation) an ATF system was started. After 118 hours of perfusion, a cell density of $29 \times 10^6$ total cells/mL was reached. At this moment a part of the cell suspension was harvested and the remaining cells were diluted with fresh medium in the 2 L bioreactor to a cell density of 16.4×10⁶ total cells/mL (82% viability, hence 13.4×10⁶ viable cells/mL). Subsequently the 2 L bioreactor was infected with Ad35.TB-S at an MOI of 70 VP/cell and incubated at 36° C., pH 7.3 and DO of 40%. The ATF system was started 15 hours post infection at a medium refreshment rate of 2 vessel volume per day. On day 1, 2, and 3 post infection the 2 L bioreactor was sampled for cell count and virus production by AEX-HPLC. To release the virus 1 mL sample was mixed with 100 μL 10% Triton X-100 and incubated at 37° C. for 30 minutes. After incubation the sample was mixed with 2.42 μL benzonase/MgCl$_2$ followed by a subsequent incubation step of 30 minutes at 37° C. Finally 100 μL 50% sucrose was added to the samples. After a centrifugation step of 5 minutes at 2500 g the samples were stored at a temperature below −65° C. until analysis by AEX-HPLC. The results are presented in Table 2.

The results demonstrated that infections at cell densities above 10×10⁶ viable cells/mL are feasible in bioreactors coupled to a perfusion system and that it is possible to increase the volumetric yield almost 10 times compared to a batch process (example 2). No premature cell loss of the infected culture was observed, indicating that the ATF process is an appropriate system for culturing infected cells.

TABLE 2

Results example 6.

| Day post infection | Cell count (×10⁶ total cells/mL) | AEX-HPLC (VP/mL) | QPA (IU/mL) | AEX/QPA (VP/IU) |
|---|---|---|---|---|
| 0 | 16.4 | NA | NA | NA |
| 1 | 21.4 | Below LOQ | Below LOQ | NA |
| 2 | 29.18 | 1.34 × 10¹² | 2.23 × 10¹¹ | 6.0 |
| 3 | 31.50 | 2.26 × 10¹² | 3.16 × 10¹¹ | 7.2 |

An FDA requirement for rAd batches is a ratio of VP/IU<30. QPA (Q-PCR based potency assay; Wang et al., 2005) analysis showed that all samples met this requirement. In contrast, the samples disclosed in Yuk et al., 2004 have a VP/IU ratio of around 100 (FIGS. 2A and 2B therein). The physical particles to infectious particles ratio is a relevant parameter for adenoviruses, and a lower ratio is preferred for rAd batches. The batches prepared in this Example consistently have such a low ratio of less than 10:1.

For a yearly demand of about 1.5×10¹⁹ VP and with a yield of about 2×10¹² VP/mL, less than 7500 L harvest has to be processed. These volumes can be processed in facilities of 1000 L or less, and would thus reduce the upfront cost commitment during vaccine development.

Example 7: Further Experiments of Infection at High-Cell Densities with a rAd35 Vector with Reduced Perfusion Rates From a PER.C6® working cell bank, cells were thawed and propagated in serum free culture medium in a humidified incubator at 37° C. and 10% CO$_2$. Subculture was performed every 3 to 4 days until sufficient cell density was reached to inoculate a 2 L bioreactor at a cell density of 0.44×10⁶ total cells/mL. Cells were propagated in the 2 L bioreactor at 37° C., DO of 40%, and a pH of 7.3. The ATF system was started 4 days post inoculation at a cell density of approximately 2.72×10⁶ total cells/mL. After 144 hours of perfusion a cell density of 30.5×10⁶ total cells/mL was reached. At this moment a part of the cell suspension was harvested and the remaining cells were diluted with fresh medium in the 2 L bioreactor to a cell density of 16.2×10⁶ total cells/mL (81% viability, hence 13.1×10⁶ viable cells/mL). Subsequently the 2 L bioreactor was infected with Ad35.TB-S at an MOI of 70 VP/cell and incubated at 36° C., pH 7.3 and DO of 40%. The ATF system was started 5 hours post infection at a medium refreshment rate of 2 vessel volume per day. On day 2, 3, and 4 post infection the 2 L bioreactor was sampled for cell count and virus production by AEX-HPLC. To release the virus 1 mL sample was mixed with 100 μL 10% Triton X-100 and incubated at 37° C. for 30 minutes. After incubation the sample was mixed with 2.42 μL benzonase/MgCl$_2$ followed by a subsequent incubation step of 30 minutes at 37° C. Finally 100 μL 50% sucrose was added to the samples. After a centrifugation step of 5 minutes at 2500 g the samples were stored at a temperature below −65° C. until analysis by AEX-HPLC. The results are presented in Table 3.

TABLE 3

Results example 7.

| Day post infection | Cell count (×10⁶ total cells/mL) | AEX-HPLC (VP/mL) | QPA (IU/mL) | AEX/QPA (VP/IU) |
|---|---|---|---|---|
| 0 | 16.19 | NA | NA | NA |
| 1 | 20.40 | NA | NA | NA |
| 2 | 24.14 | 1.42 × 10¹² | 1.77 × 10¹¹ | 8.0 |
| 3 | 24.60 | 2.20 × 10¹² | 1.82 × 10¹¹ | 12.1 |
| 4 | 16.26 | 1.90 × 10¹² | 1.51 × 10¹¹ | 12.5 |

The results again demonstrated that infections at cell densities above 10×10⁶ viable cells/mL are feasible in bioreactors coupled to a perfusion system and that it is possible to increase the volumetric yield almost 10 times compared to a batch process (Example 2). Furthermore with Examples 6 and 7, it was demonstrated that the perfusion rate after infection can be limited to 2 vessel volumes per day without compromising the virus production.

For a yearly demand of about 1.5×10¹⁹ VP and with a yield of about 2×10¹² VP/mL, less than 7500 L harvest has to be processed. These volumes can be processed in facilities of 1000 L or less, and would thus reduce the upfront cost commitment during vaccine development.

Example 8: Further Experiments of Infection at High-Cell Densities with a rAd35 Vector at 50 L Scale From a PER.C6® working cell bank, cells were thawed and propagated in serum free culture medium in a humidified incubator at 37° C. and 10% CO$_2$. Subculture was performed every 3 to 4 days until sufficient cell density was reached to inoculate a 10 L bioreactor at a cell density of 0.52×10⁶ total cells/mL. Cells were propagated in the 10 L bioreactor at 37° C., DO of 40%, and a pH of 7.3. The ATF system was started when a cell density of approximately 5.3×10⁶ total cells/mL was reached (4 days post inoculation). After 169 hours of perfusion a cell density of 77×10⁶ total cells/mL was reached. At this moment the 10 L cell suspension was diluted with fresh medium in a 50 L bioreactor to a cell density of 15.5×10⁶ total cells/mL (81% viability, hence 12.6×10⁶ viable cells/mL). Subsequently, the 50 L bioreactor was infected with Ad35.TB-S at an MOI of 70 VP/cell and incubated at 36° C., pH 7.3 and DO of 40%. The ATF system was started 5 hours post infection at a medium refreshment rate of 2 vessel volume per day. On day 2 and 3 post infection, the 50 L bioreactor was sampled for cell count and virus production by AEX-HPLC. To release the virus 1 mL sample was mixed with 100 μL 10% Triton X-100 and incubated at 37° C. for 30 minutes. After incubation, the sample was mixed with 2.42 μL benzonase/MgCl₂ followed by a subsequent incubation step of 30 minutes at 37° C. Finally, 100 μL 50% sucrose was added to the samples. After a centrifugation step of 5 minutes at 2500 g, the samples were stored at a temperature below −65° C. until analysis by AEX-HPLC. The results are presented in Table 4.

TABLE 4

Results Example 8.

| Day post infection | Cell count ($\times 10^6$ total cells/mL) | AEX-HPLC (VP/mL) | QPA (IU/mL) | AEX/QPA (VP/IU) |
|---|---|---|---|---|
| 0 | 15.5 | NA | NA | NA |
| 2 | 21.4 | $1.67 \times 10^{12}$ | $1.15 \times 10^{11}$ | 14.6 |
| 3 | 23.5 | $1.84 \times 10^{12}$ | $1.99 \times 10^{11}$ | 9.2 |

The results demonstrated that infections at cell densities above $10 \times 10^6$ viable cells/mL were feasible in 50 L bioreactors coupled to a perfusion system and that it was possible at 50 L scale to increase the volumetric yield almost 10 times compared to a batch process (example 2). It was shown herewith that the developed process could be scaled-up. The harvest volumes that must be processed per year in order to fulfill the yearly virus demand can be produced with the current process. For a yearly demand of about $1.5 \times 10^{19}$ VP and with a yield of about $2 \times 10^{12}$ VP/ml, less than 7500 L harvest has to be processed. These volumes can be processed in facilities of 1000 L or less, and would thus reduce the upfront cost commitment during vaccine development.

REFERENCES

Altaras N E, Aunins J G, Evans R K, Kamen A, Konz J O, Wolf J J. Production and formulation of adenovirus vectors. Adv. Biochem. Engin/Biotechnol. Vol. 99, 2005

Cortin V, Thibault J, Jacob D, Gamier A. High-Titer adenovirus vector production in 293S Cell Perfusion culture. Biotechnol. Prog. Vol. 20, 2004

Estape D, Wilde F. Comparison of campaign vs concurrent large-scale cell culture facilities. Pharmaceutical Engineering. Vol. 26, No. 5, September/October 2006.

Furey J. Scale-up of a cell culture perfusion process—A low-shear filtration system that inhibits filter-membrane fouling. Genetic Engineering News. Vol. 22, No. 7, April 2002.

Henry O, Doiniond E, Perrier M, Kamen A. Insights into adenoviral vector production kinetics in acoustic filter-based perfusion cultures. Biotechnology and bioengineering, Vol. 86, No. 7, June 2004.

Hodge G. Disposable bioprocessing: State of the Industry, Economics and a novel manufacturing platform case study (Presentation). NC Bio. Ctr. BPD Conference, 18 November 2004.

Kamen A, Henry O. Development and optimization of an adenovirus production process. The journal of gene medicin Vol. 6, 2004

Maranga L, Aunins J G, Zhou W. Characterization of changes in PER.C6 cellular metabolism during growth and propagation of a replication-deficient adenovirus vector. Biotechnology and Bioengineering, Vol. 90, No. 5, June 2005.

Radosevic K, Wieland C W, Rodriguez A, Weverling G J, et al. Protective immune responses to a recombinant adenovirus type 35 tuberculosis vaccine in two mouse strains: CD4 and CD8 T-cell epitope mapping and role of gamma interferon. Infect. Immun. 75: 4105-4115 (2007).

Shott J P, McGrath S M, Pau M G, Custers J H, et al. Adenovirus 5 and 35 vectors expressing *Plasmodium falciparum* circumsporozoite surface protein elicit potent antigen-specific cellular IFN-gamma and antibody responses in mice. Vaccine 26: 2818-2823 (2008).

United Nation web site: esa.un.org/unpp/index.asp?panel=2 (March 2008)

Wang F, Puddy A C, Mathis B C, Montalvo A G, et al. Using QPCR to assign infectious potencies to adenovirus based vaccines and vectors for gene therapy: toward a universal method for the facile quantitation of virus and vector potency. Vaccine 23: 4500-4508 (2005).

Xie L, Metallo C, Warren J, Pilbrough W, Peltier J, Zhong T, Pikus L, Yancy A, Leung J, Aunins J G, Zhou W. Large-Scale propagation of a replication-defective adeno vector in stirred-tank bioreactor PER.C6 cell culture under sparging conditions. Biotechnology and bioengineering, Vol. 83, No. 1, Jul. 5, 2003

Yallop C, Crowley J, Cote J, Hegmans-Brouwer K, Lagerwerf F, Gagne R, Martin J C, Oosterhuis N, Opstelten D J, Bout A. Per.C6 cells for the manufacture of biopharmaceutical proteins. Modern Biopharmaceuticals—Design, Development and Optimization. Vol. 3, 2005

Yuk I H Y, Olsen M M, Geyer S, Forestell S P. Perfusion Cultures of Human Tumor Cells: A Scalable Production Platform for Oncolytic Adenoviral Vectors. Biotechnol. Bioengin. 86: 637-641 (2004).

The invention claimed is:

1. A method for producing at least $1 \times 10^{12}$ recombinant adenovirus serotype 35 (rAd35) virus particles (VP)/mL, the method comprising:
    culturing producer cells in a first bioreactor in suspension with a perfusion system;
    transferring the cultured producer cells from the first bioreactor into a second bioreactor with a perfusion system;
    infecting the producer cells in the second bioreactor at a density of between $10 \times 10^6$ and $16 \times 10^6$ viable cells/mL with rAd35; and
    further culturing the infected producer cells in the second bioreactor to produce rAd35,
    wherein, after between about 1.5 and about 5 days, the produced rAd35 particles in the infected cell culture of the second bioreactor reach a concentration of at least $1 \times 10^{12}$ VP/mL, and the virus particle to infectious particle (VP/IU) ratio of the produced rAd35 in the infected cell culture of the second bioreactor is less than 30:1.

2. The method according to claim 1, wherein the producer cells are infected with rAd35 at a density of between about $10 \times 10^6$ and $14 \times 10^6$ viable cells/mL.

3. The method according to claim 1, wherein the producer cells are cultured with an alternating tangential flow (ATF) perfusion system after infection with rAd35.

4. The method according to claim 1, wherein the rAd35 lacks at least a portion of the E1 region of the adenovirus genome, and wherein the rAd35 comprises a heterologous nucleic acid.

5. The method according to claim 1, wherein the producer cells are cultured with an alternating tangential flow (ATF) perfusion system prior to infection with rAd35.

6. The method according to claim 1, wherein the particle to infectious particle (VP/IU) ratio of the produced rAd35 in the infected cell culture of the second bioreactor is less than 20:1.

7. A bioreactor comprising:
culture medium,
producer cells in a suspension thereof, and
at least $1 \times 10^{12}$ recombinant adenovirus serotype 35 (rAd35) virus particles/mL (VP/mL), wherein the virus particles in the infected cell culture have an infectious particle (VP/IU) ratio of less than 30:1, and wherein the bioreactor has a working volume of between 2 L and 1000 L.

8. The bioreactor of claim 7, wherein the bioreactor comprises an alternating tangential flow (ATF) perfusion system.

9. The method according to claim 1, further comprising harvesting the rAd35 virus particles from the infected producer cell culture after-between about 1.5 and about 5 days.

10. The bioreactor of claim 7, wherein the bioreactor has a working volume of between 50 L and 500 L.

11. The bioreactor of claim 10, wherein the bioreactor is connected to an alternating tangential flow (ATF) perfusion system.

12. The bioreactor of claim 7, wherein the rAd35 virus particles in the infected cell culture of the second bioreactor have a VP/IU ratio of less than 20:1.

13. The method according to claim 2, wherein the producer cells are cultured with an alternating tangential flow (ATF) perfusion system after infection with rAd35.

14. The method according to claim 2, further comprising harvesting rAd35 virus particles from the infected producer cell culture after culturing in the second bioreactor for between about 1.5 and about 5 days.

15. The method according to claim 3, further comprising harvesting rAd35 virus particles from the infected producer cell culture after culturing in the second bioreactor for between about 1.5 and about 5 days.

16. The method according to claim 9, further comprising purifying the harvested rAd35 virus particles.

17. The method according to claim 16, further comprising producing a pharmaceutical composition containing the purified rAd35 virus particles.

18. The method according to claim 14, further comprising purifying the harvested rAd35 virus particles.

19. The method according to claim 18, further comprising producing a pharmaceutical composition containing the purified rAd35 virus particles.

20. The method according to claim 15, further comprising purifying the harvested rAd35 virus particles.

21. The method according to claim 20, further comprising producing a pharmaceutical composition containing the purified rAd35 virus particles.

22. A method for producing at least $1 \times 10^{12}$ recombinant adenovirus serotype 35 (rAd35) virus particles (VP)/mL, wherein the rAd35 is replication deficient because of a deletion in the E1 region of the adenovirus genome, and wherein the producer cells complement the deletion in the E1 region, the method comprising:
culturing producer cells in suspension in a first bioreactor having an alternating tangential flow (ATF) perfusion system;
transferring producer cells from the first bioreactor to a second bioreactor having an ATF perfusion system;
infecting the producer cells at a density of between $10 \times 10^6$ and $16 \times 10^6$ viable cells/mL with rAd35; and
further culturing the infected producer cells in suspension with the perfusion system in the second bioreactor to produce rAd35 virus particles
wherein the produced rAd35 particles in the infected cell culture reach a concentration of at least $1 \times 10^{12}$ VP/mL after between about 2 and about 3 days,
wherein the producer cells produce the rAd35 virus particles with a unit productivity of between about $0.5 \times 10^5$ and $1.5 \times 10^5$ VP/cell, and
wherein the virus particle to infectious particle (VP/IU) ratio of the produced rAd35 virus particles in the infected cell culture is less than 20:1 after between about 2 and about 3 days.

23. The method according to claim 22, wherein the rAd35 comprises a heterologous nucleic acid.

24. The method according to claim 22, wherein the producer cells produce the rAd35 virus particles with a unit productivity of between $4.7 \times 10^4$ VP/cell and $1.2 \times 10^5$ VP/cell.

25. The method according to claim 1, wherein the producer cells are mammalian cells.

26. The bioreactor of claim 7, wherein the producer cells are mammalian cells.

27. The method according to claim 22, wherein the producer cells are mammalian cells.

* * * * *